United States Patent [19]

Naficy

[11] Patent Number: 4,829,055

[45] Date of Patent: May 9, 1989

[54] METHOD OF TREATMENT FOR HERPES INFECTIONS OF EXTERNAL TISSUES

[76] Inventor: Sadeque S. Naficy, 12823 Memorial Dr., Houston, Tex. 77024

[21] Appl. No.: 6,478

[22] Filed: Jan. 23, 1987

[51] Int. Cl.$^4$ .................... A61K 31/505; A61K 31/50
[52] U.S. Cl. ........................................ 514/43; 514/45; 514/46; 514/261; 514/262; 514/934
[58] Field of Search ............... 514/43, 45, 46, 261, 514/262, 934; 536/24, 26; 544/264, 276, 277

[56] References Cited

U.S. PATENT DOCUMENTS

| | | | |
|---|---|---|---|
| 4,027,025 | 5/1977 | Schaeffer | 424/251 |
| 4,060,616 | 11/1977 | Schaeffer | 424/253 |
| 4,199,574 | 4/1980 | Schaeffer | 424/200 |
| 4,211,771 | 7/1980 | Witkowski et al. | 424/180 |
| 4,294,831 | 10/1981 | Schaeffer | 424/253 |
| 4,338,310 | 7/1982 | Vince | 536/24 |
| 4,499,084 | 2/1985 | Dixon | 536/24 |
| 4,544,634 | 10/1985 | Krenitsky | 435/119 |

FOREIGN PATENT DOCUMENTS 1523865 9/1978 United Kingdom .

OTHER PUBLICATIONS

Roland K. Robins, "Synthetic Antiviral Agents" *Chemical and Engineering News* Jan. 27, 1986, pp. 28–44.
Zovirax (Acyclovir) capsules, Burroughs Wellcome Co., Jan. 1985 (package insert) 647563 Special Fold-647562.
Becker et al., J.A.M.A. Mar. 15, 1985–vol. 253, No. 11 (pp. 1601–1603).
Meyers, Infections in Surgery, Jul. 1985, pp. 531–538.
Fiumara, Infections in Surgery, Mar. 1984, pp. 225–234.
Corey, J.A.M.A., Sep. 3, 1982–vol. 248, No. 9, pp. 1041–1049.
Reichman et al., J.A.M.A., Apr. 17, 1984–vol. 251, No. 16, pp. 2103–2107.
Douglas et al., N.E. Journal of Medicine, 310: 1551–1556 (6/14/84).
Bryson et al., N.E. Journal of Medicine, 308: 916–921 (4/21/83).
Straus et al., N.E. Journal of Medicine, 310: 1545–1550 (6/14/84).

*Primary Examiner*—Joseph P. Brust
*Assistant Examiner*—MarySue Howard
*Attorney, Agent, or Firm*—Neal J. Mosely

[57] ABSTRACT

A method of treatment is disclosed for herpes infections of external tissues and method of preventing the occurrence of blisters and ulcerations in herpes disease in humans. The method consists of directly injecting small treatment amounts of suitable antiviral agents, e.g., acyclovir, ribavirin, or vidarabine (ara-A), within the specific time period of first 36 hours after the appearance of detectable manifestations of external-tissue infection or any of the prodromal symptoms of burning pain, itching, tingling, swelling and erythema or combinations thereof. The treatment amounts of antiviral drugs per day used in this invention are very small compared to the dosage amounts used by prior art calculated based on kilograms of body weight per day. The antiviral drugs so injected will kill the virus quickly in the skin or mucus membrane, or inhibit its replication or otherwise render the virus inactive before the virus will have time to multiply and form the blisters and ulcerations.

8 Claims, No Drawings

METHOD OF TREATMENT FOR HERPES INFECTIONS OF EXTERNAL TISSUES

1. Field of the Invention

This invention relates to a method of treatment of herpes infections of external tissues and method of preventing the occurrence of lesions and ulcerations in herpes, thereby method of preventing the virus shedding and spread of the disease in the population.

2. Background of the Invention

The word herpes is derived from the Greek word herepin meaning to creep. Herodotus described labial herpes associated with fever (100 AD). In 1736, John Astric described genital herpes. In 1921, Lioschultz postulated that herpes febrilis and herpes genitalis, although biologically related, they were etiologically different. This was proven to be correct in 1961, when Schneweis and Brandis demonstrated 2 different antigenic types of herpes simplex virus: Herpes virus type 1 (HSV-1) and herpes virus type 2 (HSV-2). Herpes simplex virus infections are the most ubiquitous infections of humans attacking both male and female.

The Center for Disease Control estimates that 300,000 new cases occur each year (i.e. first clinical occurrence of herpes) with a prevalence of about 25 million patients in the United States.

HERPES SIMPLEX VIRUS INFECTION: The herpes simplex virus causing infection in humans has two types: Herpes simplex type 1 (HSV-1) and Herpes simplex type 2 (HSV-2). Herpes virus can cause a wide spectrum of disease, from asymptomatic infection to severe systemic and mucocutaneous disease. Herpes virus is a DNA virus containing a molecule of deoxyribonucleic acid as its genome. The nucleic acid is encased in a protein shell and the entire infectious unit is called a virion which has a lipid-containing envelope. Virions replicate in living cells.

Infection occurs as a result of inoculation of virus through a break in the epidermal layers of skin or through the mucus membrane. Both types of herpes simplex virus penetrate the wall of the susceptible cells and interfere with the DNA configuration of the cells. The virus takes over the DNA mechanism of the cell so that the virus can replicate itself. In the process of replication of the virus, the cell is destroyed.

Type 1 herpes simplex virus usually causes the characteristic sores or blisters at the mucocutaneous junction of the lips (*herpes labialis*), nose and eyes. Type 2 herpes virus causes the same type of blisters on the male and female genitals (*herpes genitalis*) and anal area. However, the sores of type 1 and type 2 can appear at any part of the body.

It appears that once the patient is infected with HSV-1 or HSV-2, the infection is forever. Majority of HSV-2 infections are acquired sexually whereas majority of HSV-1 infections are transmitted in non-sexual ways. With both type 1 and type 2 Herpes virus there are two forms of infections: primary and latent PRIMARY OR INITIAL HERPES INFECTIONS: Initial or primary episode is more severe and more prolonged than the recurrent episodes. There are usually localized as well as generalized symptoms. Local symptoms include pain, swelling, itching, erythema and burning over areas of skin and mucus membrane of male or female genitalia. The lymph nodes in the groin area are enlarged and tender.

Generalized symptoms include fever, headache, back ache, arthralgia (pain and swelling of joints) and abdominal pain. Then the patient develops small blisters or vesicles over the skin or mucus membrane of the genitalia where the local symptoms had occurred. Some adjacent vesicles may coalesce and form one or two larger lesions. The blisters then break and form ulcerations. The ulcerated areas are red, raw and have the dermis exposed.

Whether the systemic symptoms are related to viremia, extension of viral infection, is not known. Symptoms from primary genital herpes last about 2 weeks. The healing of lesions is brought about by regeneration of epidermis and it takes about 10 to 12 days. Women seem to have more discomfort than men because of the larger surface area of involvement with coalesced, ulcerated lesions and the presence of HSV servicitis.

Primary genital HSV infection may be due to either HSV-1 or HSV-2. Clinically the acute episode is similar. However, genital HSV-1 infections do not recur as often as genital HSV-2 infections. Persons with prior HSV-1 antibody can also acquire genital HSV-2 infections. Complications of primary HSV infection include development of vesicles on other areas of the body such as buttocks, thighs and fingers which are probably due to autoinoculation. Herpes pharyngitis is a manifestation of oral genital contact and can result from HSV-1 or HSV-2. Another complication is herpes meningitis.

LATENT STAGE OF HSV INFECTIONS: Following a primary infection the virus travels along the afferent nerve to the related nerve ganglion and apparently remains there dormant for life. Herpes virus from oral herpes sequesters in the trigeminal ganglion and herpes virus from genital herpes usually gets dormant in the sacral ganglion. In about 20%-30% of the patients the virus does not reactivate and in others, recurrences may occur from time to time. Certain factors are thought to be contributing to the appearance of recurrences such as stress and the status of the immune system.

RECURRENT HERPES: The clinical manifestations of recurrent herpes lesions are preceded by prodromal symptoms such as local burning pain, tingling, itching, swelling and erythema or combinations thereof. The prodromal symptoms last a few hours to a day or two. Then in these areas of skin and mucus membrane, clusters of small blisters appear. The viral reactivation process usually occurs in a single ganglion. The virus emerges from the ganglion, travels along the nerve root to the skin or mucus membrane of the genitalia and causes the prodromal symptoms. These symptoms alert the patients that they may be having a recurrence. The inguinal lymph nodes get enlarged and tender.

Recurrent herpes lesions vary in frequency. Lesions may occur every 2 to 3 weeks or 2 or 3 times a year or never. Older people get the lesions less frequently than the young. The lesions of recurrent herpes shed virus and are infectious for about 5 days.

DIAGNOSIS: The diagnosis of primary or recurrent herpes is made by the clinical picture and laboratory tests. The morphology of the lesions preceded by the prodromal symptoms, the presence of lymphadenopathy and the pattern of the disease. Labortory diagnosis include Tzank preparation of the lesions. The lesion is scraped and the material is stained and prepared on a slide and examined under a microscope for giant cells. If multinucleated giant cells are seen then herpes virus infection is present. It could be herpes zoster or HSV.

But with sexually active patients one does not usually suspect herpes zoster infections. The sensitivity of such smears is only 50%, so negative smear does not rule out herpes.

Patients with recurrent herpes have positive neutralizing antibody tests, whereas those with primary genital herpes have a negative or low-titered blood test followed in 2 to 3 Weeks by a 4-fold or more rise in neutralizing antibody titers. The diagnosis of the latency stage is made by a neutralizing blood test for HSV-2.

The most definitive diagnostic laboratory test is isolation of virus in tissue culture. Swabs are taken from the ulcerations and sent to the virology laboratory for culture. Other tests are direct immunofluorescence (DI) and indirect immunoperoxidase (IIP) which can detect 70% of HSV infections.

PRIOR ART AND ASSOCIATED PROBLEMS
REFERENCES CITED

U.S. Patent Documents:
U.S. Pat. No. 4,199,574
U.S. Pat. No. 4,544,634
U.S. Pat. No. 4,294,831
U.S. Pat. No. 4,060,616
U.S. Pat. No. 4,027,025
U.S. Pat. No. 4,499,084
U.S. Pat. No. 4,338,610
U.S. Pat. No. 4,211,771
Foreign Patent Documents:
U.K. Pat. No. 1,523,865
Publications:
  Straus, S. E., et al. N. Engl. J. Med. 310: 1545–50, 1984.
  Bryson, Y. J., et al. N. Engl. J. Med. 308(16): 916–921, 1983.
  Mertz, G. J., et al. J.A.M.A. 252(9): 1147–1151, 1984.
  Douglas, J. M., et al. N. Engl. J. Med. 310(24): 1551–1556, 1984.
  Reichman, R. C., et al. J.A.M.A 251(16) 2103–2107, 1984.
  Corey, L., J.A.M.A. 248(9) 1041–1049, 1982.
  Fiumara, N. J., Infections in Surgery, March 1984, 225–234.
  Meyers, J. D., Infections in Surgery, July 1985, 531–538.
  Becker, T. M., J.A.M.A. 253(11) 1601–1603.
  Zovirax (Acyclovir) capsules, Burroughs Wellcome Co., January 1985 (Package Insert) 647563 Special Fold–647562.

In the prior art composition of antiviral agents are used in many different ways including: oral, parenteral (intravenous), topical as ointment, cream, powder, aerosol, eye drops or nose drops, etc. depending on whether the preparation is used to treat internal or external viral infections.

In other words the prior art makes a distinction between internal infections and external infections and for each of these two categories of infection, it uses certain routes of administration of antiviral drugs.

The prior art recommends that for internal infections the composition be administered orally or parenterally at dose levels calculated according to kilograms of body weight; and for infections of the eye or other external tissues, e.g. mouth and skin the compositions be preferably applied to the infected part of the body as a topical ointment or cream:
U.S. Pat. No. 4,199,574, column 7
U.S. Pat. No. 4,544,634, column 3
U.S. Pat. No. 4,294,831, column 7
U.S. Pat. No. 4,060,616, column 4
U.S. Pat. No. 4,027,025, column 5
U.K. Pat. No. 1,523,865, page 4
U.S. Pat. No. 4,499,084
U.S. Pat. No. 4,338,310
U.S. Pat. No. 4,211,771

The prior art considers the term parenteral to include intravenous, instramuscular, subcutaneous and intradermal, etc., and it teaches that compositions having antiviral activities can be used in these modalities. However, the prior art does not go any farther beyond these generalities and does not offer any specifications with regards to the type of virus disease or virus infection, or with regards to the location of infection in the body and the accompanied symptoms, or with regards to the timing of subcutaneous or intradermal administration or with regards to the dosage of the antiviral compositions used.

In the clinical-practice aspect of the prior art, for treatment of infections of external tissues, i.e., skin and mucus membrane, the methods of administration of antiviral drugs are: oral, intravenous, topical as ointment or cream, and drops (eye or nose drops). Antiviral agents have never been used for direct injections in the external tissues infected with herpes virus, with any specifications regarding the site of injection, the timing of injection and the treatment amounts. Antiviral drugs have never been used by prior art in the method of this invention to prevent the occurrence of blisters and ulcerations in herpes disease by local and direct injections in the infected external tissues.

The oral method is used in the prior art (clinically) for treatment of initial or primary herpes infection, for intermittent therapy of recurrences and for chromic suppressive therapy of recurrent disease. For treatment of each recurrence, the prior art recommends that oral therapy be initiated as soon as possible. For example, Burroughs Wellcome Co. recommends acyclovir capsules (Zovirax) 200 mg, 5 times daily for 5 days. However, the company in its package insert giving data on clinical studies on oral acyclovir (Zovirax capsules in doses of 200 mg or 400 mg every 4 hours, 6 times daily for 5 days) states, "Steady-state plasma levels were reached by the second day of dosing".

Considering the fact that the prodromal symptoms last only from a few hours to a day or occasionally 2 days (see BACKGROUND OF INVENTION, RECURRENT HERPES), even if the oral treatment is initiated right away, it will have no effect or very little effect during the course of the first day of therapy. By the time the steady-state of effective therapeutic levels of the antiviral agent in the plasma have been reached, the virus has already replicated, multiplied, reached the epithelial cells, formed the lesions and destroyed the cells. In other words the prior art's attempt to attack the problem comes too late.

It is because of this delay in achieving the effective therapeutic levels of the drug in the plasma, by oral method of prior art, and because of the shortness of duration of prodromal symptoms which is the golden opportunity to attack the virus, that the present invention uses direct injections within a specific period of time to quickly deliver effective antiviral drugs to the specific areas where the virus is located. By this method, practically instantly, the virus is attacked by small but necessary amounts of antiviral drugs.

The areas of skin and mucus membrane, showing prodromal symptoms, to be injected with antiviral drug are very limited. These areas may measure only from approximately 0.5 cm to 2 or 3 cm in diameter each. Thus the amounts of antiviral drug needed to deliver effective levels and concentrations of the drug to the tissues of these specific areas are very small. Therefore the possibilities of any toxicity and adverse effects are very little. Whereas in the prior art large doses of oral drugs are given which after absorption and getting diluted and spread all over the body by blood circulation, only a small fraction of the drug will reach the virus. So in the prior art, on the one hand very large amounts of antiviral drugs are used; and on the other hand it will take at least one full day for these large amounts of drugs to have any effect. In other words, the effects of the administered drugs will come too late and after the virus has already replicated and formed the lesions.

For example, using acyclovir which is the most effective drug against herpes virus, the present invention administers 1 to 6 injections in 2–4 hour intervals in the course of the 36-hour period following the appearance of the prodromal symptoms. The treatment amounts of the drug administered is 1 mg to 240 mg and preferably 30 mg to 120 mg/day. Whereas the prior art suggests a dosage of 0.01 mg to 250 mg/kg of body weight/day (7 mg to 17,500 mg for a patient weighing 70 kg). The prior art considers the optimum oral dose as being 700 mg to 1,000 mg/day. Thus the total amount of the drug for the 5-day recommended course of oral treatment of prior art will be 3,500 mg to 5,000 mg. It is obvious that such huge doses are more likely to be associated with side effects than the small doses used in the present invention.

R. Riechman et al conducted a clinical study on the treatment of recurrent genital herpes simplex infections with oral acyclovir. In this double blind study 250 patients were entered into a multi-center trial to evaluate the efficacy and toxicity of orally administered acyclovir. The study consisted of two parts; part A in which patients entered the study within 48 hours of the onset of lesions, and part B in which patient self-initiated the treatment as soon as possible after the onset of a recurrent episode. In both parts patients received either acyclovir (200 mg) or placebo, five times daily for 5 days. In both parts, the duration of virus shedding and the time to crusting and healing of lesions were shorter among acyclovir recipients than among placebo recipients.

When the investigators compared parts A and B directly the duration of virus shedding and the times required for crusting and healing of lesions were significantly shorter among acyclovir recipients in part B than among acyclovir recipients in part A.

This study demonstrates that using oral treatment, it is impossible (in intermittent therapy) to prevent the occurrence of lesions and ulcerations in the recurrences.

The chronic suppressive therapy using oral method although has some merits but it also has problems as demonstrated in the following studies:

J. Douglas et al conducted a double blind clinical study on the effects of acyclovir on suppression of recurrences of genital herpes virus infections. The study was sponsored by the National Institute of Health and Burroughs Wellcome Company. The study was conducted over 120 days on patients with frequent recurrences. While receiving therapy, 86 of 96 acyclovir-treated patients had 50% reduction of their recurrence rate. In other words recurrences could not be completely prevented.

Another clinical study was conducted by S. Straus et al from National Institute of Allergy and Infectious Diseases, NIH, and Burroughs Wellcome Company. The study was double blind and it was conducted over 125 days on 35 patients with frequently recurring genital herpes. There were significantly fewer recurrences during acyclovir treatment than during placebo treatment. All patients had recurrences after completing acyclovir treatment.

It is concluded from above two studies that oral acyclovir given for four months markedly reduces but does not completely prevent recurrences of genital herpes and does not influence the long-term natural history of the disease.

The epidemiologic problem associated with the prior art is very grave. Since as it has been demonstrated, there is always a delay of at least one day in achieving the effective therapeutic levels of the drug in plasma by oral method, the patient still goes on to develop lesions and ulcerations anyway. The ulcerations will shed virus for 3–5 days during which time the virus may be transmitted, by sexual contacts, to others and it may spread the disease in the population. But since by the method of the present invention, the lesions are prevented or substantially prevented, the spread of the disease is greatly reduced.

The intravenous (parenteral) method of therapy in the prior art is only used in patients with weak immune system and weak defense mechanism (immunocompromised) who develop severe widespread mucocutaneous herpes lesions. In this method large doses of antiviral drugs (e.g., acyclovir 5 mg/kg every 8 hours for 7 days) are administered. These doses are very large and their administration is only justified if their benefits to the patient outweigh their risk.

Since the recurrences of the herpes lesions in otherwise healthy adults are very frequent, it is not practical to hospitalize and treat the patient each time, without delay, with intravenous antiviral drugs. Nor is it safe to use such large doses of the drug so frequently.

The antiviral drugs in the form of ointment have very little effect because of the slow absorption through the skin.

SUMMARY OF THE INVENTION

It is an object of this invention to provide an effective method of treatment for herpes infections of external tissues, which will use only small amounts of antiviral drugs to treat just the infected area, and which will thereby reduce the possibility of side effects of the drugs.

It is another object of the instant invention to provide a method of administration of antiviral drugs to prevent the occurrence of lesions and ulcerations of external tissues in herpes virus infections.

It is still another object of the present invention to provide an effective method to control the herpes infection in the population by substantially preventing the occurrence of herpes virus lesions in external tissues thereby greatly reducing the virus shedding and the spread of the disease.

Other objects of the invention will become apparent from time to time throughout the specifications and claims as hereinafter related.

The above noted objects and other objects of the invention are accomplished by a method of treatment for herpes infections of external tissues and method of preventing the occurrence of blisters and ulcerations in herpes disease in humans. The method consists of directly injecting small treatment amounts of suitable antiviral agents, e.g., acyclovir, ribavirin, or vidarabine (ara-A), within the specific time period of first 36 hours after the appearance of detectable manifestations of external-tissue infection or any of the prodromal symptoms of burning pain, itching, tingling, swelling and erythema or combinations thereof. The treatment amounts of antiviral drugs per day used in this invention are very small compared to the dosage amounts used by prior art calculated based on kilograms of body weight per day. The antiviral drugs so injected will kill the virus quickly in the skin or mucus membrane, or inhibit its replication or otherwise render the virus inactive before the virus will have time to multiply and form the blisters and ulcerations.

DESCRIPTION OF THE PREFERRED EMBODIMENTS

METHOD OF APPLICATION OF INVENTION AND MECHANISM OF EFFECTS

According to the instant invention, to treat the herpes infections of external tissues, i.e., the skin and mucus membrane in a patient with herpes, the preparations of the antiviral drugs or antiviral agents are directly and locally injected in and around the areas of skin and mucus membrane which show the prodromal symptoms of impending lesions. The prodromal symptoms consist predominantly of burning, pain, itching, tingling, swelling and erythema. As soon as any one of these symptoms or any combinations of the symptoms appear on an area or areas of skin and mucus membrane, the injections are immediately administered. The injections must be given, and repeated if necessary, during the specific time period of the first 36 hours following the appearance of the symptoms.

To understand the reason why the preparations of antiviral agents should be given directly in the areas of external tissues showing evidence of infections or prodromal symptoms; and to understand the reason why they should be given during the specific time period of the first 36 hours following the appearance of the symptoms, the sequence of events whereby herpes lesions or recurrences come about should be considered.

As it was discussed in the BACKGROUND OF THE INVENTION—RECURRENT HERPES, after the primary or acute form of the disease the virus becomes latent or dormant in the nerve ganglion (sacral region in genital herpes). From time to time, the virus which is not replicating in the ganglion, by a mechanism hitherto not understood, gets mobilized from the nerve ganglion and travels along the nerve root to the relevant dermatome (area of skin and mucus membrane supplied by that nerve). When the virus arrives in the skin or mucus membrane, it causes an inflammatory reaction indicated by the prodromal symptoms. The symptoms last several hours or a day or so during which time the virus ascends to the top layers of skin (epidermis) where it multiplies and causes the small blisters or vesicles. The blisters contain large numbers of virions or full grown virus. The blisters then rupture and cause ulcerations which are moist, red, and painful. The ulcerations shed virus and are contagious.

Thus, the best time that the attack on the virus by antiviral drugs can be most effective is early in the course of the prodromal symptoms when the virus has not reached the epithelial cells and has not replicated and destroyed any cells yet. Since this critical period lasts only several hours or a day it is imperative that the attack on the virus be carried out without delay during this period of time before the virus has had a chance to replicate and form the blisters.

To achieve this, according to the method of this invention, as soon as the prodromal symptoms appear, a solution of effective and non-toxic antiviral drug or antiviral agent is injected directly under the skin and mucus membrane or in the substance of the skin and mucus membrane which show the prodromal symptoms. Depending on the involvement of the surface area or areas, a proportionate amount of the drug is injected. The solution has sufficient concentration of antiviral agent to kill or inactivate the virus or inhibit the replication of the virus without delay.

The solutions of antiviral drugs, e.g., acyclovir, ribavirin, or vidarabine (ara-A) useful for the purposes of this invention have concentrations in the range of 0.01 mg/ml to 10 mg/ml and preferably 1 mg/ml to 5 mg/ml. In each area of infection of the external tissues, depending on the surface area involved, 1 ml to 5 ml or 1 ml to 10 ml of the solution of anti-viral drug is injected or infiltrated.

Utilizing this method, small but effective amounts of antiviral drugs are delivered to the locations of the virus without having to administer large amounts of the drug either orally or parenterally.

For example, using acyclovir which is the most effective drug against herpes virus, the present invention administers 1 to 6 injections in 2–4 hour intervals in the course of the 36-hour period following the appearance of the prodromal symptoms. The treatment amounts of the drug administered are 1 mg to 240 mg and preferably 1 mg to 120 mg/day. The concentration of the antiviral agent in the infected tissues is maintained at optimum levels during the specified 36-hour period by repeating the injections, for example, every 2–4 hours as necessary to assure that the virus is killed or inactivated before having a chance to replicate and form the blisters.

The method is technically easy because the infected areas are small and on the surface of the skin and mucus membrane and are easily accessible. The method is also biologically and pharmacologically most effective, because there may be virtually no delay between the time that the symptoms are felt or recognized by the patient, and the time that antiviral drugs can be administered to the infected areas. Whereas this is not the case with the oral method which requires time for absorption and time for the drug to reach the effective therapeutic levels in the blood and the tissues in order to be effective.

Usually after the first local injection of the antiviral agent (occasionally after 2 or more injections) as the virus gets killed or inactivated the inflammatory reaction subsides and the symptoms of pain, itching, burning, etc., gradually disappear. Thus, the virus or virions having been killed, they will not be able to replicate or multiply. This means no blister formation, no rupture of blisters and no ulcerations. When ulcerations are prevented, physical pain, discomfort and sexual restrictions are prevented; and more important, virus shedding and spread of the disease in the population are prevented.

The following examples illustrate the method of application and effects of the invention in using antiviral drugs for treatment of external-tissue infection in patients with herpes recurrences.

EXAMPLE 1

Six male and female patients with genital herpes who are developing recurrences every 2-4 months are treated according to the method of the instant invention.

The patients have been previously treated by their own physicians, or at local health clinics, by oral acyclovir 200 mg 5 times daily for 5 days for each episode. Although the oral treatment shortens the duration of ulcerations and hence lessens the pain and discomfort to some extent, but the patients still develop the blisters and ulcerations nonetheless.

The patients are instructed to notify us immediately as soon as they experienced pain or itching or any combination of the familiar prodromal symptoms in the genital area. Within 6-8 hours after the appearance of symptoms 10 ml of a solution of acyclovir containing 7 mg/ml is directly injected in the areas of skin or mucus membrane which is swollen, red, itching, and painful. After 4 hours another dose of 10 ml acyclovir solution 7 mg/ml is administered. Within 4-6 hours after the first injection the burning pain starts to subside, and within 24-48 hours, swelling, erythema and other symptoms gradually disappear. There is no blister formation and the skin and mucus membrane do not break or ulcerate. The recurrences are completely aborted.

EXAMPLE 2

Four male patients are treated for the recurrences of genital herpes using the method of the present invention.

Within 4-6 hours after the onset of the prodromal symptoms a solution of 5 mg/ml acyclovir is injected directly in the areas with prodromal symptoms. A total of 5 ml of acyclovir solution is administered to each patient. A repeat injection of 5 ml of the same solution of acyclovir is given after 2 hours. No other injections are given. Pain, burning and itching start to subside within 6-8 hours after the first injection. Swelling and erythema gradually disappear within 36-48 hours. There is no blister formation and no ulceration.

EXAMPLE 3

In this group there are 7 patients who are very reliable and highly motivated. It is decided to initiate the local injections of acyclovir without significant lapse of time after the appearance of symptoms. Vials of sterile powder of acyclovir, sterile saline solution and small syringes with hypodermic needles are supplied to these patients. They are instructed and taught as to how to prepare the acyclovir solution and administer it to themselves like injection of insulin in diabetics.

All of the 7 patients administer the first dose of 5 mg/ml acyclovir in 2-3 hours after they experience the first symptoms in genital area. They inject a total of 3-7 ml of acyclovir solution depending on the surface area with pain, itching, swelling etc. They do not administer a second injection.

In this group of patients pain and itching starts to subside very rapidly, within 3-4 hours after the injection; and all other symptoms virtually disappear within 24-36 hours. Thus, the recurrences are aborted and no lesions develop.

EXAMPLE 4

Five patients who are developing herpes recurrences every 1 to 3 months are treated with local injections of vidarabine solution. However, in these patients repeated injections have to be given due to the low solubility of vidarabine in water.

In these patients, within 3-6 hours after the appearance of prodromal symptoms, 10 ml of 0.45 mg/ml solution of vidarbine in sterile water is directly injected to each patient in and around the areas showing itching, pain, burning or any combination of the familiar prodromal symptoms. Injections are repeated every 2 hours for 4 times.

The burning pain and itching starts to subside within 12-18 hours after initial injection. However, because of repeated injections, the swelling (a great deal of which due to the introduced volume of solution in the tissues) takes a relatively long time to subside (2-3 days and in come patients even longer). The patients do not develop blisters or ulcerations.

EXAMPLE 5

Four herpes patients frequently developing recurrences are treated with a composition of antiviral drug containing vidarabine, DMSO (Dimethyl Sulfoxide), as a carrier agent, and demineralized water.

In these patients within 4-8 hours after the appearance of any of the prodromal symptoms, the antiviral composition containing 5 mg/ml vidarabine is injected to the patients, in the areas showing the prodromal symptoms. 10 ml of the composition is administered to each patient. Injections are repeated 2 times in 4-hour intervals. Within 8-10 hours after the first injection, pain and itching starts to disappear but the swelling takes 2-3 days to subside. The recurrences are aborted and there are no blisters or ulcerations.

EXAMPLE 6

Three patients who are developing herpes recurrences every 1-3 months are treated with an antiviral composition containing vidarabine 7 mg/ml, demineralized water and DMSO.

In these patients within 3-7 hours after the appearance of any of the prodromal symptoms on the skin or mucus membrane, 6 ml of the vidarabine composition is administered to these areas. The injections are repeated after 4 hours. No other injections are given. Burning pain and itching start to subside within 6-7 hours after the first injection and within 36-48 hours the swelling and other symptoms gradually disappear. There are uo blister formation or ulcerations.

While this invention has been described fully and completely with special emphasis upon a preferred embodiment, it should be understood that within the scope of the appended claims the invention may be practiced otherwise than as specifically described herein.

I claim:

1. A method of treatment for herpes infections of external tissues including skin and mucus membrane in humans, comprising the steps of injecting or infiltrating, small doses, in an effective amount in the range of 1 ml to 10 ml of a solution of an antiviral drug effective in the treatment of herpes virus having a concentration of 0.01 mg/ml to 10 mg/ml only in and around said areas of infetion of external tissues;

said injection or infiltration being administered in 1 to 6 injections at 2-4 hour intervals, as needed, during the specific time period of first 36 hours after the appearance of detectable manifestations of infections of said external tissues;

said treatment amounts of said antiviral drugs being just sufficient to provide effective therapeutic concentrations in said infected external tissues; without producing a steady state of therapeutic levels of antiviral agents in the serum or blood or other tissues; and thus using necessary treatment amounts of said antiviral drugs per day substantially less than conventional dosage amounts per day calculated based on kilograms of body weight.

2. A method according to claim 1 wherein
said herpes infections are caused by herpes simplex virus type 1 (HSV-1) or herpes simplex virus type 2 (HSV-2) or varicella-zoster virus.

3. A method according to claim 1 wherein
said anti-viral drug or agent is acyclovir, ribavirin, or vidarabine (ara-A).

4. A method of preventing the occurrence of herpes lesions and ulcerations of external tissues including skin and mucus membrane, comprising the steps of
injecting or infiltrating small doses, in an effective amount in the range of 1 ml to 10 ml of a solution of an antiviral drug effective in the treatment of herpes virus having a concentration of 0.01 mg/ml to 10 mg/ml in the substance of skin and mucus membrane or under the skin and mucus membrane;

said treatment amounts being administered only in and around the areas of skin and mucus membrane showing the prodromal symptoms, or early detectable manifestations of external tissue-infection and impending lesions, consisting predominantly of itching, pain, swelling, erthema, tingling and burning sensation, or combinations thereof;

said injections or infiltrations being administered in 1 to 6 injections at 2-4 hour intervals, as needed, during the specicic time period of first 36 hours after the appearance of any of said prodromal symptoms, and in treatment amounts of said antiviral drugs just sufficient to provide effective therapeutic concentrations in said infected external tissues without producing a steady state of therapeutic level of antiviral drugs in the serum or blood or other tissues;

whereby the necessary treatment amounts of said antiviral drugs per day being far less than conventional dosage amounts per day calculated based on kilograms of body weight.

5. A method of treatment according to claim 4 in which
said antiviral drug is acyclovir, ribavirin, or vidarabine (Ara-A).

6. A method of treatment according to claim 5 wherein
the antiviral drug is acyclovir.

7. A method of treatment according to claim 5 wherein
the antiviral drug is ribavirin.

8. A method of treatment according to claim 5 wherein
the antiviral drug is vidarabine (ara-A).

* * * * *